United States Patent
Bell et al.

(10) Patent No.: US 11,348,695 B2
(45) Date of Patent: May 31, 2022

(54) MACHINE LOGIC FOR RECOMMENDING SPECIALIZED FIRST AID SERVICES

(71) Applicant: International Business Machines Corporation, Armonk, NY (US)

(72) Inventors: Denise Bell, Austin, TX (US); Cristina Bonanni, Rome (IT); Anupam Panda, Contai (IN); Tathagato Bose, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 208 days.

(21) Appl. No.: 16/826,494

(22) Filed: Mar. 23, 2020

(65) Prior Publication Data

US 2021/0296009 A1 Sep. 23, 2021

(51) Int. Cl.

| | |
|---|---|
| *G06F 15/16* | (2006.01) |
| *G16H 80/00* | (2018.01) |
| *G16H 40/40* | (2018.01) |
| *H04W 4/029* | (2018.01) |
| *G06F 9/54* | (2006.01) |
| *G16H 40/20* | (2018.01) |

(52) U.S. Cl.
CPC .......... *G16H 80/00* (2018.01); *G06F 9/542* (2013.01); *G16H 40/20* (2018.01); *G16H 40/40* (2018.01); *H04W 4/029* (2018.02)

(58) Field of Classification Search
None
See application file for complete search history.

(56) References Cited

U.S. PATENT DOCUMENTS

| | | | |
|---|---|---|---|
| 6,735,477 B2 | 5/2004 | Levine | |
| 7,052,468 B2 | 5/2006 | Melker | |
| 9,158,304 B2 | 10/2015 | Fleck | |
| 9,254,099 B2 | 2/2016 | Connor | |
| 9,324,120 B2 | 4/2016 | Braun | |
| 9,529,385 B2 | 12/2016 | Connor | |
| 9,602,993 B2 | 3/2017 | Vilrokx | |
| 9,736,630 B2 | 8/2017 | King | |
| 10,565,845 B1* | 2/2020 | Beyer | H04W 4/16 |
| 2006/0293572 A1* | 12/2006 | Bulat | A61B 5/7465 600/300 |
| 2008/0175898 A1 | 7/2008 | Jones | |
| 2015/0359489 A1* | 12/2015 | Baudenbacher | G16H 40/67 600/300 |
| 2016/0100302 A1 | 4/2016 | Barash | |
| 2016/0174857 A1 | 6/2016 | Eggers | |
| 2016/0260328 A1 | 9/2016 | Mishra | |
| 2017/0151959 A1* | 6/2017 | Boesen | A61B 5/6803 |

(Continued)

FOREIGN PATENT DOCUMENTS

| | | |
|---|---|---|
| CN | 100546509 C | 10/2009 |
| CN | 107945459 A | 4/2018 |
| WO | 2018169634 A1 | 9/2018 |

*Primary Examiner* — Brian Whipple
*Assistant Examiner* — Gregory P Tolchinsky
(74) *Attorney, Agent, or Firm* — David B. Woycechowsky (57) ABSTRACT

Technology for locating medical supplies, medical practitioners and/or non-medical-practitioner individuals who are in proximity to a first user who is experiencing a medical emergency. Appropriate notifications of and/or to the proximate medical supplies, medical practitioners and/or non-medical-practitioner individuals are made over a communication network.

2 Claims, 4 Drawing Sheets

(56) References Cited

U.S. PATENT DOCUMENTS

| | | | |
|---|---|---|---|
| 2017/0242428 A1* | 8/2017 | Pal | A61B 5/021 |
| 2018/0174261 A1* | 6/2018 | Brabazon | G16H 80/00 |
| 2018/0218124 A1* | 8/2018 | Gorelick | G16H 10/65 |
| 2018/0278894 A1* | 9/2018 | Kanga | G06K 9/00369 |
| 2018/0314798 A1* | 11/2018 | Hernandez | G16H 50/20 |
| 2018/0366220 A1* | 12/2018 | Liao | G16H 40/40 |
| 2019/0359220 A1* | 11/2019 | Wilson | G05D 1/0088 |
| 2019/0385753 A1* | 12/2019 | Aganyan | G16H 10/60 |
| 2020/0082917 A1* | 3/2020 | Kumar | G06Q 50/30 |
| 2020/0187150 A1* | 6/2020 | Eisner | H04W 64/003 |
| 2021/0098116 A1* | 4/2021 | Srivathsa | G06Q 10/0633 |
| 2021/0107523 A1* | 4/2021 | Lacaze | G06N 3/08 |

* cited by examiner

MACHINE LOGIC FOR RECOMMENDING SPECIALIZED FIRST AID SERVICES

BACKGROUND

The present invention relates generally to the field of medical care, and more particularly to the use of computers to dispatch medical care in an emergency.

The Wikipedia entry for "medical alarm" (as of 1 Mar. 2020) states, in part, as follows: "A medical alarm is an alarm system designed to signal the presence of a hazard requiring urgent attention and to summon emergency medical personnel. Other terms for a medical alarm are Personal Emergency Response System (PERS) or medical alert. Typical systems have a wireless pendant or transmitter that can be activated in an emergency. When the medical alarm is activated, the signal is transmitted to an alarm monitoring company's central station, other emergency agency or other programmed phone numbers. Medical personnel are then dispatched to the site where the alarm was activated. Elderly people and disabled people who live alone commonly use/require medical alarms. . . . Hormann's concept of "home alert" (Hausnotruf) is thus to be seen as fairly broad, including the communication of biomedical data and social communication, and not limited to use as an 'elder alarm' . . . . There are several different types of medical alarm providers: . . . Full service companies that provide installation, ongoing education and periodic testing programs . . . Individually coordinated services that rely on a smart phone app to communicate alerts to a list of personal contacts. . . . There are a number of different devices that can be used to trigger an alarm. . . . Installed motion detectors in a home . . . Radar based detectors in a room . . . A smart phone . . . Active devices require the user to take some action to trigger an alarm condition; passive systems monitor the user and raise an alarm based on an algorithm—a fall, lack of activity, etc. A weakness of active devices is that the user must be conscious to trigger the alarm. Both passive and active devices require that the user wear the device. Installed systems can be expensive and difficult to deploy. . . some systems will transmit the GPS location of the alarming device . . . some systems can be configured to transmit additional personal information when an alarm is triggered (such as age, medical history, etc.) . . . Responders [may include] Class-B EMT Operators . . . local 911 service . . . friend(s) or family . . . A Florida State University research team is currently working on an Android device to be worn by the user that not only can be used as a typical medical alert monitoring system but has fall detection software built into it. The system is designed to monitor the user's location, position, and movement in the event a fall occurs." (footnotes omitted)

SUMMARY

According to an aspect of the present invention, there is a method, computer program product and/or system that performs the following operations (not necessarily in the following order): (i) registering a plurality of medical supply sources; (ii) receiving notification of a medical emergency being experienced by a first user; (iii) receiving first user location data indicative of a geographic location of the first user; (iv) determining a current location of a most proximate medical supply store of the plurality of medical supply stores; and (v) taking an action to help get medical supplies from the most proximate medical supply store to the geographic location of the first user.

According to a further aspect of the present invention, there is a method, computer program product and/or system that performs the following operations (not necessarily in the following order): (i) registering a plurality of medical practitioners; (ii) receiving notification of a medical emergency being experienced by a first user; (iii) receiving first user location data indicative of a geographic location of the first user; (iv) determining a current location of a most proximate medical practitioner of the plurality of medical practitioners; and (v) taking an action to help get the most proximate medical practitioner to the geographic location of the first user.

According to a further aspect of the present invention, there is a method, computer program product and/or system that performs the following operations (not necessarily in the following order): (i) registering a plurality of persons; (ii) receiving notification of a medical emergency being experienced by a first user; (iii) receiving first user location data indicative of a geographic location of the first user; (iv) determining a current location of a proximate set of person(s) to the geographic location of the first user; and (v) sending a first instructional video to the set of proximate non-medical-practitioners.

DETAILED DESCRIPTION

PRELIMINARY DISCLAIMER REGARDING MEDICAL INFO PRIVACY: some embodiments of the present invention may collect and use medical information of users; this kind of data collection: (i) should only be done with knowing and voluntary consent of the users involved; and (ii) must follow all applicable privacy laws and/or regulations of all applicable jurisdictions (for example, nations of the users, nations to which the medical data is communicated.

This Detailed Description section is divided into the following subsections: (i) The Hardware and Software Environment; (ii) Example Embodiment; (iii) Further Comments and/or Embodiments; and (iv) Definitions.

I. THE HARDWARE AND SOFTWARE ENVIRONMENT

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be anything made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semi-conductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
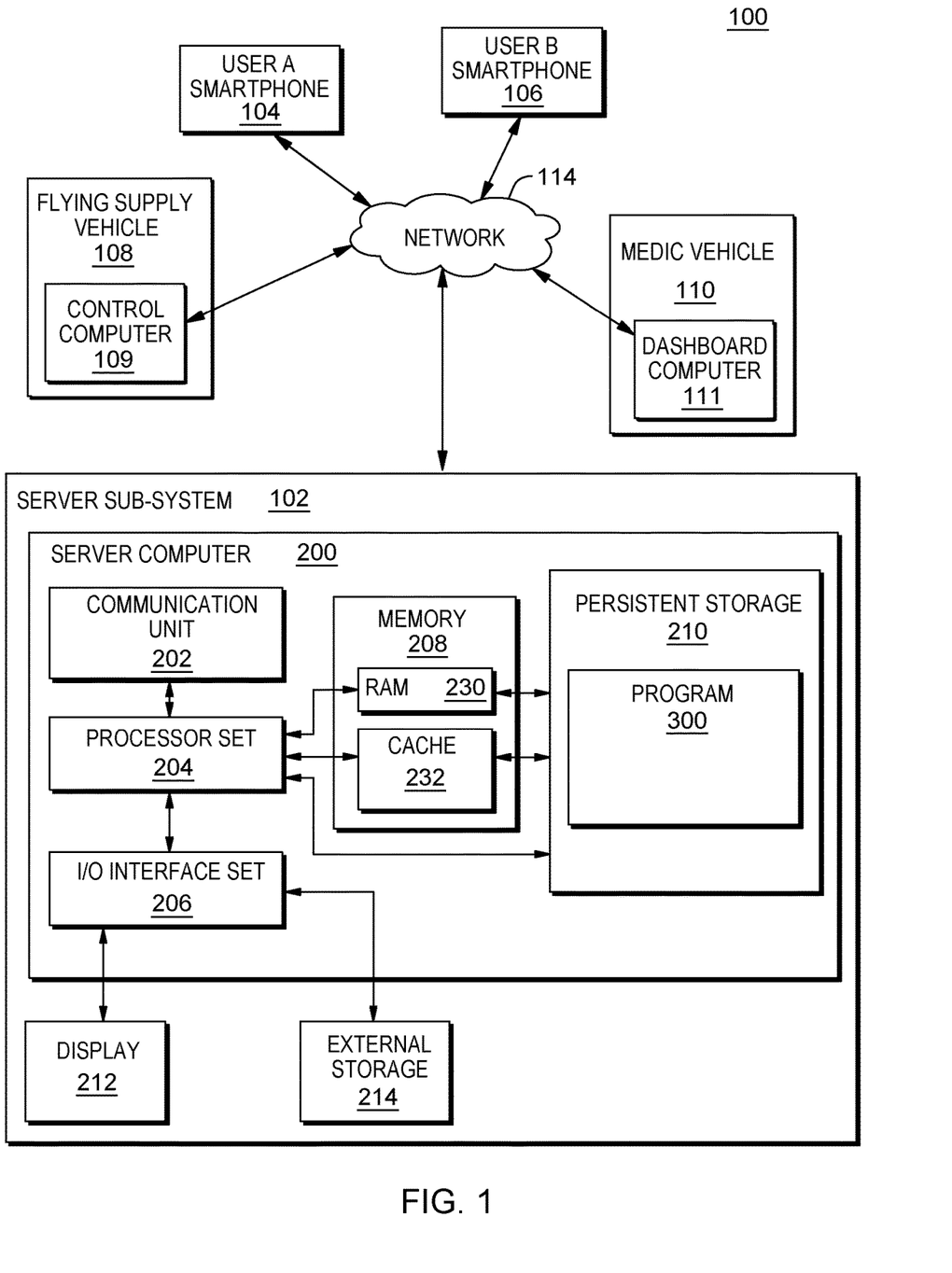
FIG. 1 is a block diagram view of a first embodiment of a system according to the present invention.

As shown in FIG. 1, networked computers system 100 is an embodiment of a hardware and software environment for use with various embodiments of the present invention. Networked computers system 100 includes: server subsystem 102 (sometimes herein referred to, more simply, as subsystem 102); user A smartphone 104; user B smartphone 106; flying supply vehicle 108 (in this example, an unmanned aerial vehicle (UAV) that includes control computer 109); medic vehicle 110 (in this example a driverless car including dashboard computer 111); and communication network 114. Server subsystem 102 includes: server computer 200; communication unit 202; processor set 204; input/output (I/O) interface set 206; memory 208; persistent storage 210; display 212; external device(s) 214; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. EXAMPLE EMBODIMENT

Figure 2:
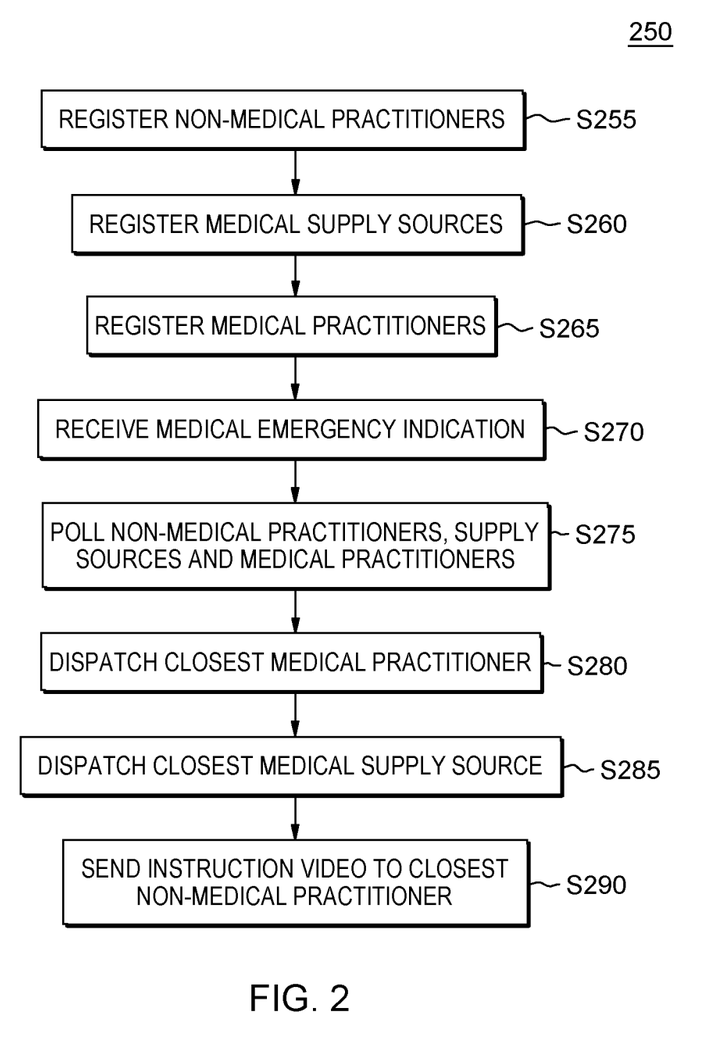
FIG. 2 is a flowchart showing a first embodiment method performed, at least in part, by the first embodiment system.
Figure 3:
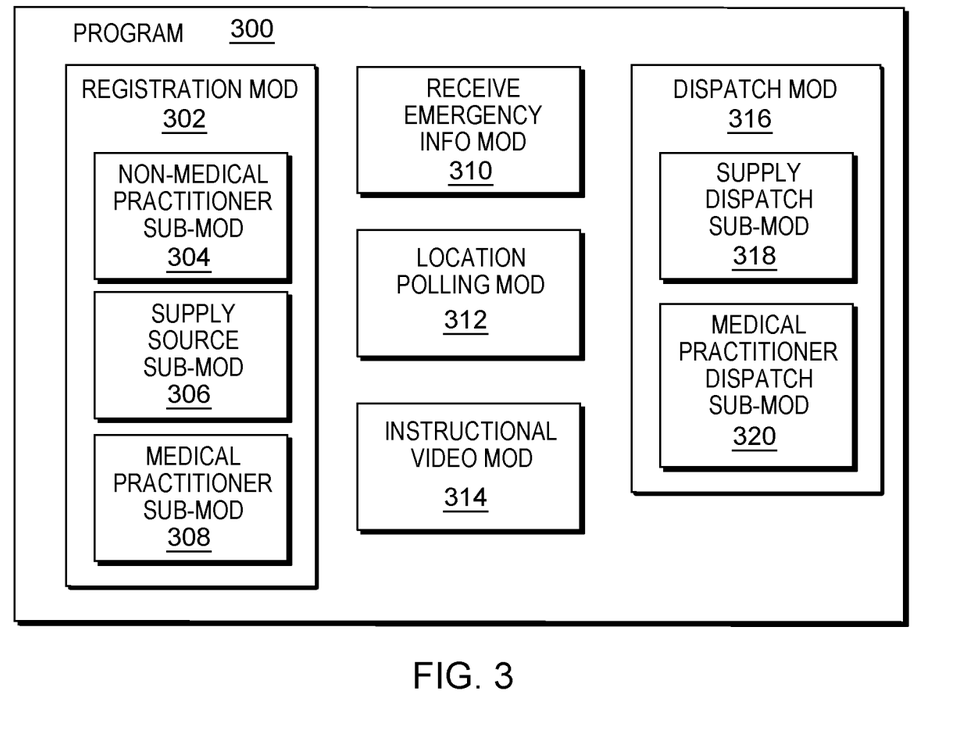
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or controls performance of at least some of the method operations of flowchart 250. This method and associated software will now be discussed, over the course of the following paragraphs, with extensive reference to the blocks of FIGS. 1, 2 and 3.

Processing begins at operation S255, where non-medical practitioner sub-mod 304 of registration module ("mod") 302 registers non-medical practitioners with an enhanced emergency medical service according to the present invention. In this example, the enhanced service is provided in exchange for a monthly service fee. The non-medical-practitioners are people from all walks of life, but what they have in common is that they do not necessarily have any special medical training. In this example, as part of the enhanced service, the non-medical-practitioners agree to try to provide aid to other service subscribers to the extent that they may be called upon (see discussion of operation S290, below) and are able. Two of the non-medical-practitioner service providers in this example are: (i) user A who registers through user A smartphone 104 and communication network 114; and (ii) user B who registers through user B smartphone and communication network 114. In this embodiment, the non-medical practitioner users do not give any particular medical information to the emergency medical service provider. Alternatively, and as discussed below in the next sub-section of the Detailed Description section, the users may provide various types of medical information so that the nature of their respective medical emergencies can be more accurately monitored for and determined.

Processing proceeds to operation S260, where supply source sub-mod 306 registers various medical supply sources that are accessible by the emergency medical service provider. In this example, the medical supply sources take the form of four (4) UAV's, each of which carries the following medical supplies as it roams the service coverage area: (i) insulin for diabetics; (ii) epi pens for allergic attacks; and (iii) tourniquet kits for lacerations. Alternatively and/or additionally, the medical supplies could be stored in stationary locations and/or other types of vehicles. As will be further discussed in the following sub-section of this Detailed Description section, the various types of medical supplies may have a great variety. In this example, one of the four (4) UAV's is flying supply vehicle 108, which registers through its control computer 109 and communication network 114.

Processing proceeds to operation S265, where medical practitioner (or medic) sub-mod 308 registers people with medical training. In this example, these medical practitioners get the emergency medical service for free as long as they agree to be on call for a certain number of hours a week, during which time they respectively ride around in a fleet of driverless vehicles. One of these driverless vehicles is medic vehicle 110. Medic vehicle 110 registers through its dashboard computer 111 and communication network 114. Each medic must be trained to respond to at least three kinds of medical emergencies: (i) a diabetic coma (sometimes herein called a "CODE 1"); (ii) an allergy attack (sometimes herein called a "CODE 2"); and (iii) a laceration (sometimes herein called a "CODE 3").

Figure 4:
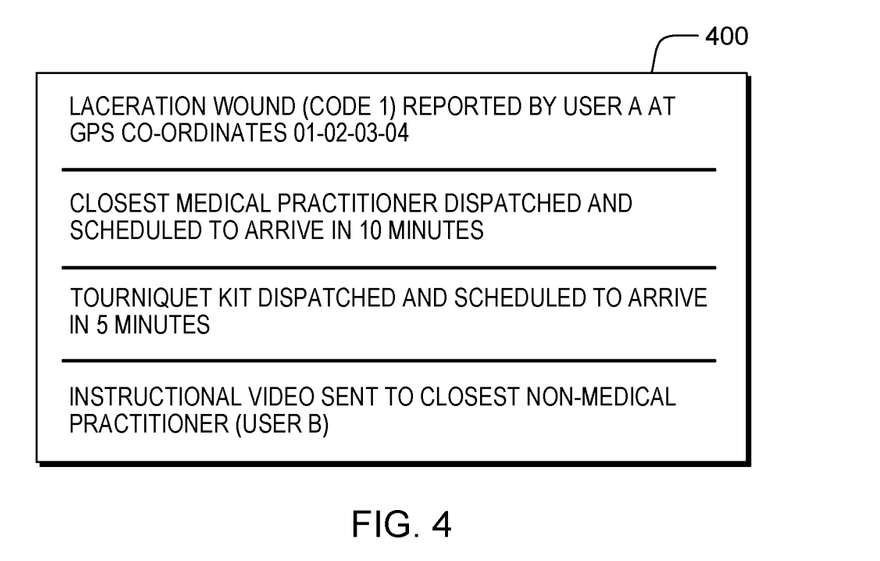
FIG. 4 is a screenshot view generated by the first embodiment system.

Processing proceeds to operation S270, where user A smartphone 104 sends a notification through communication network 114 and to receive emergency info mod 310 that user A is experiencing a medical emergency in the form of a laceration (see also screenshot 400 of FIG. 4). In addition to the notification of the type of medical emergency (in this example, a CODE 3), user A smartphone also sends the GPS (global positioning system) data to indicate where user A and her smartphone are located. This embodiment is a passive embodiment, meaning that it is up to the user having the medical emergency to communicate the type of emergency being experienced (in this example a CODE 3), but the GPS data indicative of user A's location is automatically added by machine logic. Alternatively, and as will be discussed in the next sub-section of this Detailed Description section, some embodiments are active in that the detection and communication of the emergency is performed automatically by machine logic.

Processing proceeds to operation S275, where location polling mod 312 polls the locations of: (i) registered medic vehicles to find the closest medic vehicle to the location of user A smartphone 104 (in this example, the closest vehicle is medic vehicle 110); (ii) registered supply UAVs to find the UAV to the location of user A smartphone 104 (in this example, the closest UAV is flying supply vehicle 108); and (iii) registered non-medical practitioners to find the closest non-medical practitioner to the location of user A smartphone 104 (in this example, the closest non-medical-practitioner is user B, the owner of user B smartphone 106). It is noted that in some embodiments, some, or all, of the eligible medics and/or medic supplies may not be located in autonomous vehicles (for example, they may be in offices). This embodiment polls for locations only after a new medical emergency is reported. Alternatively, other embodiments may monitor the locations of medical supply sources, medics and/or non-medic users intermittently even when there is no emergency. Also, when medical supplies and/or medics are at fixed locations, the polling may be trivial in that the server sub-system may already have the location information, which does not change, from back when the medical resource first registered.

Processing proceeds to operation S280, where medical practitioner dispatch sub-mod 320 of dispatch mod 316 dispatches medic vehicle 110 to the location of user A through communication network 114 and dashboard computer 111. The medic in the vehicle is notified of the new assignment and begins her ablutions so that she will be ready to treat user A's laceration (CODE 3) as soon as she arrives on the scene. As shown in screen shot 400 of FIG. 4, the medic is predicted to arrive on the scene in ten (10) minutes.

Processing proceeds to operation S285, where supply dispatch sub-mod 318 of dispatch mod 316 dispatches flying supply vehicle 108 to the location of user A through communication network 114 and control computer 109. As shown in screen shot 400 of FIG. 4, the supplies (most pertinently, a tourniquet kit) is predicted to arrive on the scene in five (5) minutes.

Processing proceeds to operation S290, where instruction video mod 314 sends to user B smartphone 106: (i) a notification of the CODE 3 emergency in her close proximity; and (ii) an instructional streaming video on how to treat a laceration with a tourniquet kit. In this way, even non-medical practitioner, user B, will be ready to apply a tourniquet as soon as the flying supply vehicle gets there, and, notably, five (5) minutes before the medic is scheduled to arrive.

III. FURTHER COMMENTS AND/OR EMBODIMENTS

When a patient experiences a medical emergency, it may be important for the patient to receive medical care as quickly as possible. First aid can provide valuable assistance to the patient until trained medical services are available. In some cases, the first people to manage medical care or assistance are non-trained medical personnel. For example, the chance that a patient's heart can be successfully defibrillated increases significantly if a defibrillation pulse is applied quickly.

Some embodiments of the present invention may include one, or more, of the following operations, features, characteristics and/or advantages: (i) recommending and/or providing fast and specialized first aid services; (ii) communicate to a vehicle, or autonomous machines, by transmitting GPS location and code for the kind of medical supplies needed; (iii) efficiently provides emergency needs to a person at the times of medical situations; (iv) includes a step by step algorithm (described below) to provide help to a person with medical needs; (v) when an emergency occurs, the system generates and broadcasts an alert containing the emergency GPS coordinates and the code associated with the kind of medical supplies needed; (vi) the system transmits the code using communication technology such as mobile telephone communication, WLAN (wireless local area network), NFC (near field communication), Bluetooth, or, optical signals; (vii) the closest autonomous machine containing the needed tools is activated for joining the emergency place; (viii) a request of help message is also sent to the app of the mobiles of the closest individuals such as paramedics, emergency medical technicians, police officers and others trained for example in defibrillation techniques (as mentioned above, the chance that a patient's heart can be successfully defibrillated increases significantly if a defibrillation pulse is applied quickly); (ix) at the time a call to an ambulance with specialized doctors in that disease is generated; and/or (x) the application running on the patient personal device (such as a smartwatch, phone), and communicating with the smartwatches/phones of the people around her, suggests the recovery steps be performed in that specific situation with audio and images.

Some embodiments of the present invention may include one, or more, of the following operations, features, characteristics and/or advantages: (i) locates a variety of different autonomous machine for rapid delivery of medical supplies and medications, including specific substances in the environment; (ii) each autonomous machine (for example, "medical items") is associated with different emergency situations with a specific code and different kinds of medications can be located on the same autonomous machine; (iii) in that case, the system uses the code to identify the closest autonomous machine and some kind of indicator will mark the specific medication to be used; (iv) the people that receive the alert for helping in the emergency are selected based on the proximity and their specialization; (v) a system for providing the quickest first aid with the most appropriate tools and personnel; and/or (vi) based on a system where people and the related conditions and disabilities are certified/captured and tracked.

Further to item (vi) in the list of the previous paragraph, some related conditions and disabilities that may be certified and tracked include: allergies, pregnancy, heart disease, diabetes and epilepsy. In some embodiments, this data is stored both in a central database and on the patient's device (for example, smartwatches or mobile) together with the current health values status. In some embodiments, this status is based on the information collected by the devices and other environmental sensors (of device and/or sensor types now known or to be developed in the future): blood pressure, body activities, recent physical activity, climbing, speed, duration, hours of sleep, perspiration/body temperature, quantity of alcohol and cigarettes and/or kind of food, current medications. This data will be used to identify the medical support that is needed and help locate the closest resources, such as: medications, equipment and certified or trained people subscribed to the application for providing emergency assistance when available in the emergency proximity.

Some embodiments of the present invention may include one, or more, of the following operations, features, characteristics and/or advantages: (i) having the tools to recognize an emergency, to assess it and find the fastest and most specialized first aid is essential to take immediate action and prevent the situation from becoming worse; (ii) includes a component that performs a method to identify "fastest first aid"; (iii) uses a 360-detection system (person has fallen, people around, speech around analyzed) that alerts of an emergency and by spreading out different medical autonomous machines in the environment (for example, transporting defibrillators, oxygen masks, blood bank, different types of medications and so on) mapped with specific codes corresponding to the different kinds of alerts; (iv) includes a component that performs a method to identify "specialized first aid"; and/or (v) combines certified sickness (for example, heart patient, epilepsy patient, pregnant woman, diabetic, allergic person, and so on) with the current health status (for example, blood pressure, temperature, heart rate frequency, presence of sweat) detected by the patient's smartwatch and by the environment sensors (of types now known or to be developed in the future).

In some embodiments, when a medical emergency occurs, the mobile application can detect the emergency by analyzing the data collected by the patient personal devices and the patient's environment sensors. In some embodiments, a smartwatch can send an alert if the patient is no longer walking (GPS coordinates remain the same or falling is detected by using gyroscope. In some embodiments, proximity sensors detect the concentration of people around the patient. In some embodiments, the system starts analyzing keywords in the speech of the people around that position (all keywords concerning emergency situations such as help, doesn't move, burnt, he is swollen, he is trembling and so on). In some embodiments, depending on the certified disease, and current health values, the system detects the kind of emergency such as a heart attack, dangerous arrhythmias, an anaphylactic shock, pregnancy problems, hypoglycemic crisis and so on. For example, if the certified status is pregnancy and there is a blood pressure quickly decreasing, the system identifies the probable reason for this situation. In some embodiments, to speed up the first aid, the app has machine logic that locates a variety of different autonomous machines for rapid delivery of medical supplies and medications, including specific substances in the environment. Each autonomous machine (for example, "medical items") is associated with different emergency situations with a specific code.

In some embodiments, when an emergency occurs: (i) the system generates and broadcasts an alert containing the emergency GPS coordinates and the code associated with the kind of medical supplies needed; (ii) the system transmits the code using communication technology such as mobile telephone communication, WLAN, NFC, Bluetooth, or, optical signals; and (iii) the closest autonomous machine containing the needed tools is activated for joining the emergency place. Some examples of "needed tools" are as follows: defibrillator for a heart attack, oxygen mask for the difficulty in breathing, a set of medications (for example cortisone for allergic persons or medicines for epilepsy if the certified disease is epilepsy), and/or different kinds of medications can be located on the same autonomous machine. In some embodiments, the system uses the code to identify the closest autonomous machine and indicator could be used to mark the specific medication to be used.

In some embodiments, a call to an ambulance with specialized doctors for a condition or disease, that a user is known to have, is generated by machine logic when certain triggering conditions are met. In some embodiments, the application runs on the patient personal device (such as a smartwatch, phone) and communicates with the smartwatches/phones of the people around her to suggest to these bystanders the recovery steps that may be performed in that specific situation with audio and images. Some examples of this audio/video instruction may include: how to use the defibrillator in a heart attack, how to use an oxygen mask, medication dosage requirements and/or other considerations. In some embodiments, a request of help message is also sent to the app of the mobiles of the closest individuals such as paramedics, emergency medical technicians, police officers and others trained for example in defibrillation techniques. In some embodiments, these people have previously subscribed to the application to make their data, the kind of help they can provide, available to a central database (see medical privacy info disclaimer, above). In some embodiments, aids are sent and made available exclusively to people in the proximity that are doctors or that have a first-aid certificate.

Figure 5:
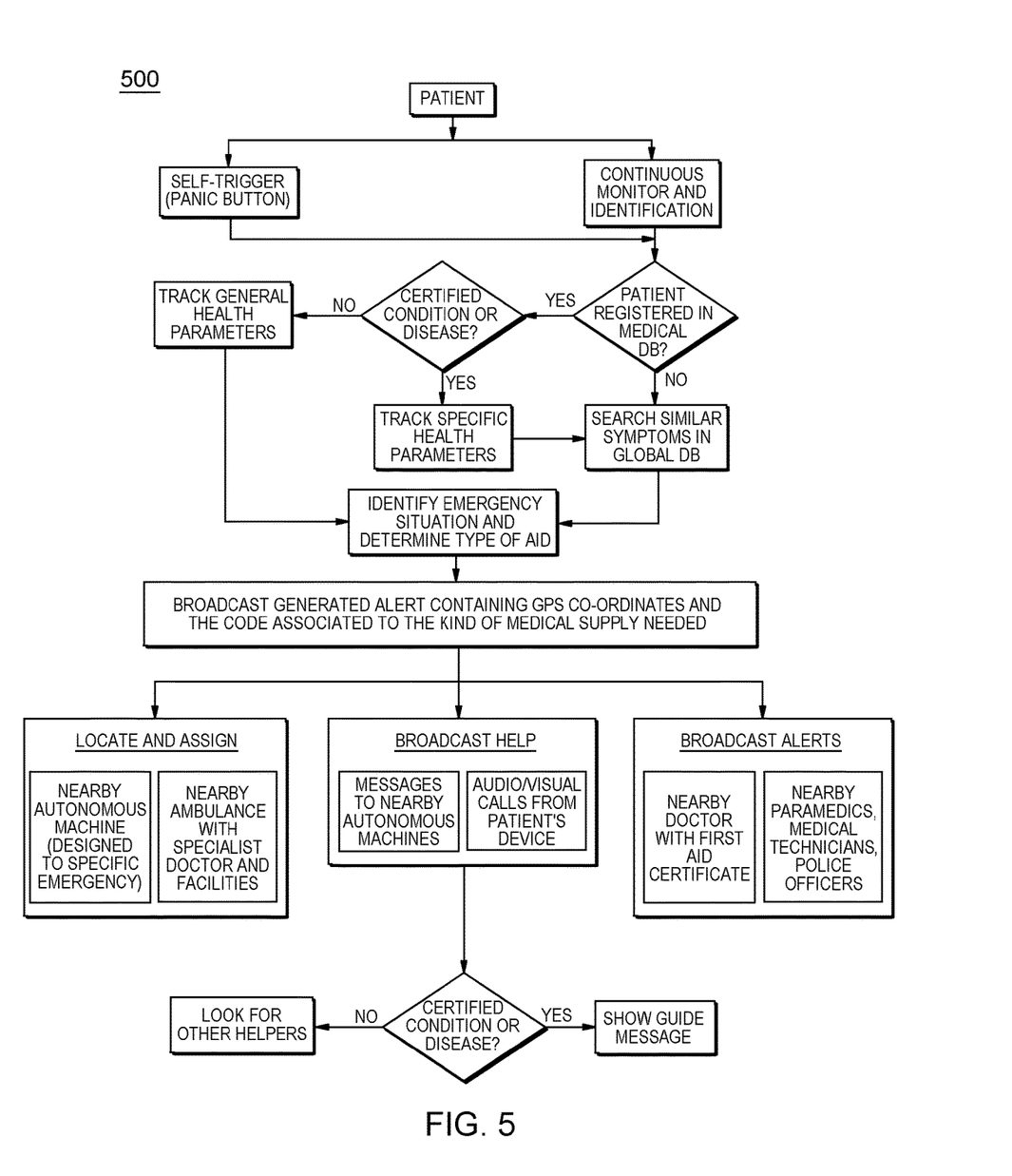
FIG. 5 is a flowchart showing a second embodiment method according to the present invention.

As shown in flow chart 500 of FIG. 5, depending on a detected type of emergency a different code is generated, that code identifies the type of medical supply needed.

Some embodiments of the present invention may include one, or more, of the following operations, features, characteristics and/or advantages: (i) managing the interaction among medical devices, medical practitioners and nearby non-medical-practitioner individuals with mechanism of tagging and metadata etc. based services and clusters; (ii) using the knowledge of both global database and the person specific record and environment data to assess the situation in hand and taking the right decision and improving the process over the time; (iii) deciding the selection of helpers in the proximity based on tag and rank of qualification on performing the task at hand; (iv) selecting the first level data from global database where user will be registering themselves with particular skills with credential proofs; and/or (v) if the first level does not find anyone qualified enough for the specific first aid it will move to level two where it will query the social media data of the persons about their medical skills in the proximity range, if it fails in this stage it will keep on increasing the proximity range up to a certain threshold.

Some embodiments of the present invention may include one, or more, of the following operations, features, characteristics and/or advantages: (i) end to end automation scope; (ii) answers certain situations such as what if no experts found within the proximity range or how the person who needs help has special needs based on the person specific record or application working accuracy models; (iii) an integrated system where the endpoint starts with the user's wearable devices which identify the critical situation based on general health parameter as well as person-specific health issues, maintained in database; (iv) every registered user has unique id associated with all the devices and record associated with them; (v) in an emergency, the device raises an alarm with all the required data to the centralized control system which refers to the global database for the registered users currently available in the close proximity as well as the specialists, ambulance, equipment, medicines etc.; (vi) all instruments and specialists are geo tagged in advance as well as analyzing their current location which to determine which instruments and specialists are in proximity to an emergency when the medical emergency is detected; (vii) person specific knowledge about an individual's health history; (viii) emphasis upon a specific health condition that requires emergency attention on certain situation (for example, for a pregnant person or person having allergies may need special attention based on certain situations tracked by the 360 monitoring system to help pin point the issue at hand more accurately); (ix) the helpers are of different kinds but they all have some important roles to play; (x) a layperson can coordinate the things or in case of unavailability of any expert he/she can perform some life saving measures; (xi) on the other hand specialists are also informed parallelly along with ambulance in the close proximity based on their distance tag (both registered and live location); (xii) if the nearest first level of helper is having expertise in performing life saving measures (decided by the global DB (database) knowledge as well as social media data) that individual will be considered as the expert first aid provider and will be communicated for detailed information about the emergency; (xiii) includes an algorithm of searching specialist in the proximity based on their prior registered data in the global DB and contingency strategy(ies) for case empty returns; (xiv) multiple aspects of first aid providing mechanism including reinforcement learning model for improving the overall applications selection accuracy as well as maintaining a global database of user specific data to map specific situation need; and/or (xv) 360 detection system that analyzes various surrounding elements such as speech analysis of people surrounding/environmental element levels, etc.

Some embodiments of the present invention may include one, or more, of the following operations, features, characteristics and/or advantages: (i) includes a multi-faceted features of an integrated system that includes not only reinforcement learning model but fall back mechanism(s) in case of unavailability of specialist within the proximity of emergency and also referring to a global database for specific details; (ii) uniform tags are assigned; (iii) the person seeking emergency aid will be associated with a type of issue that he/she is going through; (iv) includes person specific medical information (for example, person specific medical records); (v) emergency demonstration presentation to a layperson in case no available specialists are found; (vi) includes a 360 detection system for current environmental status as well as user specific medical record for identifying the kind of emergency and best life saving measures to offer; (vii) an automated and integrated system where various factors will play key role in deciding the correct action; (viii) improvement model(s) and algorithm(s) to search and assign specialist as well as lay person; (ix) selecting the first level data from global database where user will be registering themselves with particular skills with credential proofs; (x) if the first level does not find anyone qualified enough for the specific first aid it will move to level two where it will query the social media data of the persons about their medical skills in the proximity range; (xi) if it fails in the first attempt at performing the second stage it will keep on increasing the proximity range up to a certain threshold; (xii) has multiple layers, including audio-visual guide for using medical devices to a laymen to reinforcement learning model and maintaining user specific medical data; (xiii) a 360 monitoring system which will also take the speech of the needy person and the people surround them as well as factors such as smoking; (xiv) people are assigned based on their level of expertise; and/or (xv) in case of a no availability of specialists then a lay person can continue with life saving act(s).

IV. DEFINITIONS

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer-implemented method (CIM) comprising:
   registering a plurality of autonomous vehicles that contain medical items, with each given autonomous vehicle of the plurality of autonomous vehicles being assigned a code indicative of the identity of the medical items contained in the given autonomous vehicle;
   distributing the plurality of autonomous vehicles over a geographic area;
   receiving notification of a first medical item needed to help with a first medical emergency being experienced by a first user;
   receiving first user location data indicative of a geographic location of the first user;
   determining a current location of a first autonomous vehicle, of the plurality of autonomous vehicles, that is the most proximate autonomous vehicle that contains the first medical item based on the codes assigned to the autonomous medical vehicles of the plurality of autonomous medical vehicles; and
   instructing the first autonomous vehicle to travel to the geographic location of the first user.

2. The CIM of claim 1 further comprising:
   detecting, by a 360-detection system, the first medical emergency.

* * * * *